United States Patent [19]
Chen et al.

[11] Patent Number: 5,721,104
[45] Date of Patent: *Feb. 24, 1998

[54] SCREENING ASSAY FOR ANTI-HIV DRUGS

[75] Inventors: Irvin S. Y. Chen, Woodland Hills; Jeremy B. M. Jowett; Vicente Planelles, both of Los Angeles, all of Calif.

[73] Assignee: Regents of the University of California, Los Angeles, Calif.

[*] Notice: The portion of the term of this patent subsequent to Jun. 17, 2011, has been disclaimed.

[21] Appl. No.: 485,694

[22] Filed: Jun. 7, 1995

Related U.S. Application Data

[63] Continuation of Ser. No. 322,750, Oct. 13, 1994.

[51] Int. Cl.$^6$ .................. G01N 33/53; G01N 33/567
[52] U.S. Cl. .................. 435/7.1; 435/7.2; 435/7.21
[58] Field of Search .................. 435/7.2, 7.21, 435/7.1

[56] References Cited

FOREIGN PATENT DOCUMENTS

| WO 91/19817 | 12/1991 | WIPO . |
| 9419456 | 9/1994 | WIPO . |
| WO 94/19456 | 9/1994 | WIPO . |

OTHER PUBLICATIONS

Balotta, C., Antisense Phosphorothioate Oligodeoxynucleotides Targeted to the vpr Gene Inhibit Human Immunodeficienc Virus Type 1 Replication in Primary Human Macrophages, *J. Virol* (1993) 67:4409.

Cohen, E.A. et al. Identification of HIV–1 vpr Product and Function, *J AIDS* (1990) 3:11–18.

Cohen, E.A. et al. Human Immunodeficiency Virus vpr Product Is a Virion–Associated Regulatory Protein, *J Virol* (1990) 64:3097–3099.

Gras-Masse, H. et al. A Synthetic Protein Corresponding to the Entire vpr Gene Product from the Human Immunodeficiency virus HIV–1 is Recognized by Antibodies from HIV–Infected Patients, *Int J Pept Prot Res* (1990) 36:219.

Hattori, N. et al. The Human Innumodeficiency Virus Type 2 vpr Gene is Essential for Productive Infection of Human Macrophages, *Proc Natl Acad Sci USA* (1990) 87:8080–8084.

Heinzinger, N.K. et al. The Vpr Protein of Human Immunodeficiency Virus Type 1 Influences Nuclear Localizatioin of Viral Nucleic Acids in Nondividing Host Cells, *Proc Natl Acad Sci USA* (1994) 91:7311–7315.

Lang, S.M. et al. Importance of vpr for Infection of Rhesus Monkeys with Simian Immunodeficiency Virus, *J Virol* (1993) 67:902–912.

Lavallee, C. et al. Requirements of the Pr55$^{gag}$ Precursor for Incorporation of the Vpr Product into Human Immunodeficiency Virus Type 1 Viral Particles, *J Virol* (1994) 68:1926.

Levy, D.N. et al. Induction of Cell Differentiation by Human Immunodeficiency Virus 1 vpr, *Cell* (1993) 72:541.

Ogawa, K. et al. Open Reading Frame *J Virol* (1990) 63:4110–4114.

Paxton, W. et al. Incorporation of Vpr into Human Immunodeficiency Virus Type 1 Virions: Requirement for the p6 Region of gag and Mutational Analysis, *J Virol* (1993) 67:7229–7237.

Pianelles et al., Manuscript: "Vpr–Induced Cell Cycle Arrest is Conserved Among Primate Lentiviruses", University of Alabama at Birmingham, Division of Hematology and Oncology (date not available).

Reiss, P. et al. Antibody Response to Viral Proteins U (vpu) and R (vpr) in HIV–1–Infected Individuals, *J AIDS* (1990) 3:115.

Tristem, M. et al. Evolution of the Primate Lentiviruses: Evidence form vpx and vpr, *EMBO J* (1992) 11:3405.

Yu, et al. Open Reading Frame vpr of Simian Immunodeficiency Virus Encodes a Virion–Associated Protein, *J Virol* (1990) 64:5688.

Yuan et al., *AIDS Research and Human Retroviruses*, vol. 6, No. 11, issued 1990, "Human Immunodeficiency Virus vpr Gene Encodes a Virion–Associated Protein", pp. 1265–1271.

*Primary Examiner*—Keith D. Hendricks
*Attorney, Agent, or Firm*—Morrison & Foerster LLP

[57] ABSTRACT

The essential role of the Vpr protein of HIV in the progression of HIV infection is disclosed. Recognition of this role permits assay for potential drug candidates by virtue of their ability to interfere with the interaction of Vpr with its intracellular targets. Thus, cells that are modified to contain an expression system for the production of Vpr are cultured in the presence and absence of the drug candidate and the growth rates compared. The ability of a candidate to enhance the growth of a culture producing Vpr indicates its potential as an anti-AIDS therapeutic.

6 Claims, 2 Drawing Sheets

SCREENING ASSAY FOR ANTI-HIV DRUGS

This application is a continuation of application Ser. No. 08/322,750 filed 13 Oct. 1994.

ACKNOWLEDGEMENT OF GOVERNMENT SUPPORT

The work described herein was funded in part by a grant from the National Institutes of Health No. C930122. The U.S. government has certain rights in this invention.

TECHNICAL FIELD

The invention relates to methods for screening drug candidates that will be effective in arresting the progress of HIV infection and Acquired Immune Deficiency Syndrome (AIDS). More specifically, it concerns assays based on the ability of drug candidates to interfere with the interaction of the HIV encoded protein Vpr with its intracellular targets.

BACKGROUND ART

The human immunodeficiency virus (HIV) is believed to effect the development and progress of AIDS through infection of $CD4^+$ T cells, macrophage and other lymphoid and nonlymphoid cell types that contain this marker. The population of $CD4^+$ cells is generally used as a measure of AIDS progression, since $CD4^+$ cells are continuously depleted in the course of the disease. The mechanism of $CD4^+$ cell depletion has not been elucidated; however, the major cytolytic effect of HIV infection on $CD4^+$ cells in culture is an envelope-mediated syncytium induction. Other mechanisms which may be effective in vivo include stimulation of the production of cytokines, clearance of HIV-infected cells by cytotoxic lymphocytes and autoimmune mechanisms, and apoptosis.

Based on general concepts of the mechanism of retroviral infection and the nature of the infected cell, three types of drugs to arrest the progress of AIDS have been proposed. One class contains those which block reverse transcription such as azidothymidine (AZT), another class comprises protease inhibitors that prevent maturation of the virions, and the third class comprises drugs such as soluble CD4 which prevent interaction between the virion and the CD4 receptor. The efficacy of each of these classes of drugs is limited, and there is clearly a need for more effective ways to arrest the progress of this condition.

The approach of the present invention takes advantage of the critical role of the HIV-encoded protein Vpr. Vpr is one of nine proteins known to be encoded by the HIV genome. A diagram of the HIV genome, shown schematically, is set forth in FIG. 1. Vpr was initially identified as an open reading frame in the HIV genome. Expression of this open reading frame was confirmed by the demonstration that individuals infected with HIV develop antibodies against the Vpr gene product (Gras-Masse, H. et al. *Int J Pept Prot Res* (1990) 36: 219; Reiss, P. et al. *J AIDS* (1990) 3: 115. The gene product was shown to be weak transcriptional activator by Cohen, E. A. et al. *J AIDS* (1990) 3: 11–18 and by Ogawa, K. et al. *J Virol* (1990) 63: 4110–4114. The protein appears to be present in virions at an equimolar amount compared to the major gag-encoded capsid proteins and has been shown to interact with the gag-encoded protein p6. Cohen, E. A. et al. *J Virol* (1990) 64: 3097–3099, Yu, et al. *J Virol* (1990) 64: 5688; Yuan, X. et al. *AIDS Res Cum Retro* (1990) 6: 1265; Paxton, W. et al. *J Virol* (1993) 67: 7229; Lavallee, C. et al. *J Virol* (1994) 68: 1926. For interaction with p6, the carboxy terminal amino acids at positions 84–94 are required. Paxton, W. et al. *J Virol* (supra).

The human HIV Type 2 Vpr gene has been shown as essential for productive infection of human macrophage by Hattori, N. et al. *Proc Natl Acad Sci USA* (1990) 87: 8080–8084; however, Balotta, C. *J Virol* (1993) 67: 4409 has shown Vpr to be unnecessary for replication of the virus in immortalized T cell lines or peripheral blood lymphocytes. The Vpr protein has been shown to provide a mechanism for nuclear localization of viral nucleic acids in nondividing cells by Heinzinger, N. K. et al. *Proc Natl Acad Sci USA* (1994) 91: 7311–7315. In addition, Lang, S. M. et al. *J Virol* (1993) 67: 902–912 have shown that mutations in Vpr attenuate the pathogenicity of macagues infected with SIV. Further, Tristem, M. et al. *EMBO J* (1992) 11: 3405 showed that Vpr and Vpx are highly conserved among primate lentiviruses. Levy, D. N. et al. *Cell* (1993) 72: 541 demonstrated that Vpr induces differentiation and growth arrest in human rhabdomyosarcoma cells.

It is therefore known that Vpr is not a null protein with respect to infection by HIV. However, the central role played by this protein in permitting virus to multiply while effecting depletion of the very cells which are infected by the virus has not been appreciated. The present applicants have demonstrated that Vpr arrests the development of cells in which it is contained at the G2 stage of the life cycle. Arrest at this particular point is significant since HIV integration occurs during the previous S phase of the cell cycle. Also, preventing the cells from entering the subsequent mitotic stage (M) prevents infected cells from entering the GO stage in which the relative metabolic inactivity of the cells would be unfavorable for adequate viral production. Furthermore, arrest of cells in the G2 stage may prevent apoptosis thus, also, permitting continued viral production. Importantly, it also prevents T cell clonal expansion.

The Vpr protein and its interaction with intracellular targets in the infected cell are crucial to the success of the infective virus. Therefore, therapeutic agents which interrupt this interaction will also successfully arrest the progress of the disease.

DISCLOSURE OF THE INVENTION

By recognizing the critical role of Vpr protein in effecting arrest of cell development in the G2 stage, and by demonstrating that this effect is observable in cells modified to contain the Vpr protein, but which are not necessarily infected with HIV, the invention provides convenient screening tools for the identification of successful candidate drugs that have high potential for being efficacious in the treatment of AIDS.

Thus, in one aspect, the invention is directed to methods to screen candidate AIDS-combative drugs which method comprises culturing cells which have been modified to contain an expression system for a nucleotide sequence encoding the Vpr protein under conditions wherein the nucleotide sequence encoding the Vpr protein is expressed in the presence and absence of said candidate. The growth of the cultures in the presence and absence of said candidate is measured; and compared. Enhanced growth in the presence of said candidate as compared to growth in its absence indicates potential as an anti-AIDS therapeutic. The difference in growth rates may result from an effect of the candidate on the Vpr protein per se or, and in the alternative, from the interaction between the candidate and an intracellular target.

The invention is also directed to recombinant materials useful in the assay systems of the present invention, including recombinant expression systems for the Vpr protein containing inducible control sequences, host cells and cell lines modified to contain these expression systems, and vectors for the introduction of such expression systems into host cells.

MODES OF CARRYING OUT THE INVENTION

Figure 1:
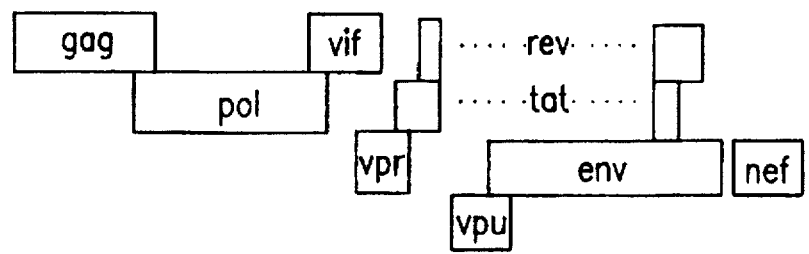
FIG. 1 is a diagram of the HIV genome showing the location of the coding region for the Vpr protein.

The invention provides assay systems designed for straightforward testing of candidate drugs for the treatment of AIDS. The systems take advantage of the critical role played by the Vpr protein in the arrest of infected cell development at the G2 stage after integration of the HIV genome and prior to mitosis.

As used herein, "Vpr protein" refers to the 94-amino acid protein encoded by the HIV-1 virus as described by Cohen et al. *J Virol* (1990) 64: 3097 as well as the corresponding protein derived from other HIV strains. Vpr protein also includes minimally modified forms of this protein or subunits thereof which retain the ability to arrest the cell cycle at the G2 stable. It is well understood that minor modification can be made to the amino acid sequence of proteins without altering, dramatically, their activity. Preferred modifications include substitution of conservative amino acids for those in the wild-type protein in noncritical regions. Minimal numbers of substitutions are preferred. In addition, it is also understood that the primary amino acid structure may be derivatized to, for example, sugars, lipids, acyl groups, and the like. Such modifications which do not interfere with the G2-arresting function of Vpr are also contemplated. Furthermore, the complete amino acid sequence may not be necessary for the requisite activity. Thus, fragments of the wild-type Vpr which remain active are also included.

In general, "Vpr" as used in the present context, includes any altered forms of wild-type Vpr proteins which remain useful in the method of the invention. The test for ascertaining such utility is straightforward; the modified form need only be tested in comparison to wild type for its ability to arrest cells at the G2 stage or, more simply, to inhibit growth when expressed in mammalian or other eucaryotic cells.

Of course, the effect of potential drug candidates on the ability of HIV to effect G2 arrest in infected cells could be measured directly using the flow cytometry techniques described in Example 1 below by conducting these assays in the presence and absence of the candidate and detecting a shift in the G2/G1 ratio. However, this approach suffers from a number of disadvantages, similar to those involved in using screening techniques to search for AIDS-effective compounds in general, rather than those, necessarily, that effect G2 arrest. First, there are the inherent biohazards in working with the infective virus. Second, only a small percentage of the cells treated will become infected, leading to results that are difficult to interpret. Finally, because the G2/G1 ratio is focused upon specifically, flow cytometric techniques are required; these techniques are inappropriate for routine quick screening assays.

Since it has been found that the Vpr protein can effect G2 arrest not only in cells infected with or susceptible to infection with HIV, but in any cell in which it is produced, assay systems can be designed which are independent of the hazards of the virus and which permit rapid measurement of the effect of the Vpr protein on cell growth in general. Because vectors can be designed to stably insert an expression system for Vpr into recombinant host cells, cell lines can be created which are capable of producing Vpr protein throughout the culture. For cell lines that have been stably modified to be capable of producing Vpr, it is greatly preferable to construct such expression systems using control sequences that comprise promoters that are inducible by manipulation of culture conditions, since constitutive expression of Vpr would inhibit the replication of the cell line.

In broad outline, the assays of the invention comprise providing cells, preferably those of a cell line, which have been modified to contain an expression system for the HIV-encoded Vpr protein. For transient expression, such as in COS cells, the nature of the expression system is not especially critical; however, if a cell line which stably contains the genetic materials for Vpr expression is desired, the expression system should be one wherein the expression of the Vpr protein is under the control of an inducible promoter. The cells are first cultured to growth phase; for cell lines containing the Vpr expression system, this must be done under conditions wherein the promoter is not induced. The conditions are then altered to effect induction of expression in control cultures without the test compound and test cultures in the presence of the test compound. The control cultures will fail to grow effectively; the cultures maintained in the presence of a successful test compound will continue replicating. Thus, compounds which are capable of maintaining the replication of the modified cell line wherein Vpr production has been induced are excellent candidates for use in AIDS therapies.

A variety of recombinant constructs can be used to modify the host cells. Mammalian host cells are preferred, such as COS-7 cells, HeLa cells, CHO cells, $GH_3$ cells, $GH_4$ cells and the like. Expression systems and vectors compatible with these cells are well known in the art including expression systems which employ viral promoters such as the SV40 promoter, adenovirus promoter and the like as well as retroviral vectors containing LTR promoters. However, for the reason set forth above, the use of inducible promoters is preferred in the case of stably transformed cell lines. Inducible promoters, such as the metallothionein promoter, steroid hormone-controlled promoters, the tetracycline-controlled minimal CMV promoter and the like are also known in the art. Gossen, M. et al. *Proc Natl Acad Sci USA* (1992) 89: 5547–5551; Resnitzky, D. et al. *Mol Cell Biol* (1994) 14: 1669–1679.

While mammalian cells are preferred, any cell for which the Vpr has a common effect can also be used, such as yeast cells or bacterial cells. Suitable expression systems including promoters and appropriate additional control signals are also well known for use in yeast and bacterial cells. Insect cells are also candidates for the host cells useful in the invention; the bacculovirus system is most conveniently used in the case of insect cells.

The host cells are modified using techniques appropriate to the vector on which the expression system resides. If desired, homologous sequences can be used to effect integration of the expression system into the genome of the transfected cells. Embryonic stem cells or fertilized eggs could be used as well to create transgenic mammals for use as in vivo models for therapeutic testing.

Thus transgenic animals can be produced which contain expression systems in their germline with the Vpr nucleotide sequence under the control of an inducible promoter. The animals can be used in test protocols by activating the promoter and testing the effects of candidate therapeutic agents.

Once a cell line has been prepared capable of expressing the Vpr gene, the test compound can be screened as described generally above using a variety of criteria to indicate growth arrest. Flow cytometry techniques are not excluded, however the growth status of cells using less complex techniques can be determined as described below. In standard culture conditions, a number of indices of cell growth can be used, such as labeled thymidine uptake, vital stains such as Alamar blue, trypan blue and the like, cell number as measured by the density of culture or with a cell counter or spectrophotometer, indicators of growth parameters such as pH of culture medium; detection of cell byproducts; kinase assays such as the immunoprecipitation of cdc2 kinase; assay of WEE 1, NIM 1, CAK, and phosphates; and levels of cyclin mRNA expression.

In addition, certain genes are known to be expressed specifically in particular phases of the cell cycle such as M, G1 and S. Assessment of the level of expression of these genes will provide a measure of the status of the cells in culture. For example, the cells may be transfected with promoters associated with these specifically expressed genes, such as CDK or cyclin, wherein the promoter is operably linked to a specific reporter gene such as chloramphenicol acetyl transferase (CAT) or luciferase.

The foregoing assay systems are possible because Vpr is effective in arresting the cell cycle for cell types in general, especially eucaryotic cells, more particularly vertebrate cells, still more particularly mammalian cells, primate cells or human cells. Since Vpr has this capacity, it may be used to control unwanted cell proliferation in general, such as in the treatment of malignancies or autoimmune diseases. The Vpr protein can itself be administered to a subject in need of such treatment using appropriate formulations for the administration of protein-based drugs.

The following examples are intended to illustrate but not to limit the invention.

EXAMPLE 1

Verification that HIV Infection Results in G2 Arrest

Cell flow cytometric techniques were used to determine a DNA histogram for SupT1 cells, both for cells that were mock-infected and those infected with the HIV-1 strain NL4-3.

SupT1 cells (human CD4$^+$ T cell), derived from a non-Hodgkins lymphoma (NIH, AIDS research and reference reagent program; Cat. No. 100) were passaged in RPMi 1640 media supplemented with 10% fetal calf serum (FCS; Gemini, Calabasas CA Cat. No. 100-106), penicillin (100 U/ml), streptomycin (100 µg/ml) and 2 mM glutamine (Irvine Scientific, Santa Ana, Calif. Cat. No. 9316).

Viral stocks of the strain, HIV-1 NL4 3 (Adachi, A. et al. *J Virol* (1986) 59: 284–291) were generated by electroporation of MT-2 cells. MT-2 cells, a human HTLV-1 transformed T cell line (NIH AIDS research and reference reagent program Cat. No. 237), were propagated in Iscove's media (Gibco-BRL; Cat. No. 12440-038) supplemented with 10% FCS and antibiotics as above.

Briefly, 5×10$^6$ MT-2 cells were collected midlog phase, pelleted at 300 g and resuspended in electroporation medium (RPMI with 20% FCS). Plasmid pNL 4-3 (10 µg; Adachi, A. et al. (1986) (supra)), was added, incubated on ice for five minutes, electroporated at 960 uF and 300 V, incubated on ice for a further five minutes, and finally resuspended in 20 ml of growth medium. At six to eight days post-transfection culture supernatant was harvested and assayed for infectious virus titer by limiting dilution assay and for HIV core antigen (p24) by enzyme-linked immunoabsorbant assay (ELISA; Coulter). Viral stocks were stored at −70° C. until use.

Target SupT1 cells, 5×10$^6$, were infected by suspension in viral stock and 10 µg/ml polybrene (Sigma, St Louis, Mo. Cat. No. H-9268) at 37° C. for one hour, with gentle agitation. Cells were washed and resuspended finally at 5×10$^5$ cells/ml in growth medium and analyzed by flow cytometry.

Cell cycle phase analysis of a bulk population of cells was determined by staining in a hypotonic citrate solution containing propidium iodide (P1, Sigma, St Louis, Mo. Cat. No. P 4170) as previously described (Nicoletti, L. et al. *J Immun Meth* (1991) 139: 271–280. Briefly, 1×10$^6$ cells were harvested from the culture and suspended in 1 ml of the staining solution (100 µg P1 in 0.1% sodium citrate plus 0.1% Triton X-100 (Sigma, St. Louis, Mo. Cat. No. T-6878) and 20 µg ribonuclease A (Sigma, St. Louis Mo. Cat. No. R-5503). After incubation on ice for 1 hour, the cells were analyzed in the staining solution on a FACScan flow cytometer (Becton Dickinson) equipped with a 15 mW air-cooled 488 nm argon-ion laser. Orange P1 fluorescence was collected after a 585/42 nm band pass (BP) filter and was displayed on linear scale. Acquisition on the flow cytometer was done with either FACScan Research software or Lysis II (Becton Dickinson). A minimum of 5000 events was collected per sample, and data analysis performed with Lysis II software. Samples were gated on low angle (forward scatter, FSC) vs. 90° angle (side scatter, SSC) to exclude debris and clumps. Additionally samples were collected using the CellFit acquisition and analysis program (Becton Dickinson), for comparison.

Figure 2B:
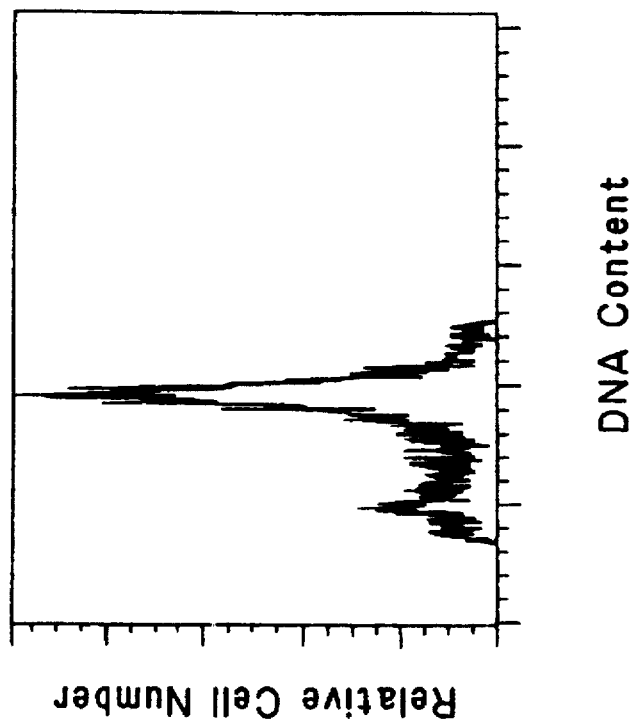
FIG. 2 shows the G2 arrest pattern effected by HIV infection as determined by flow cytometry.
Figure 2A:
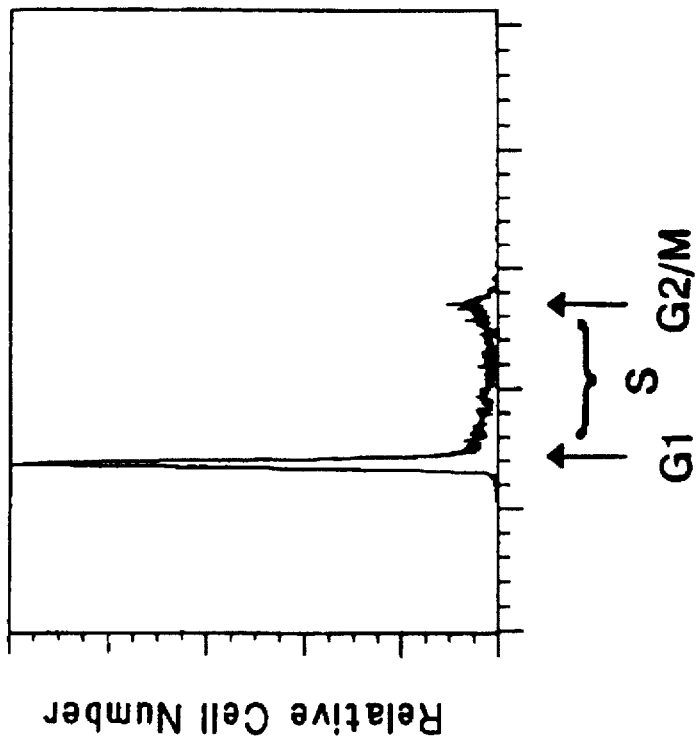

FIG. 2 shows a comparison of the histograms obtained. As shown in FIG. 2, the mock-infected cells are mostly concentrated in the G1 phase whereas those infected with HIV are concentrated in phase G2. The ratio of cells in G1 as compared to G2/M was 2.5 for mock-infected cells and 0.35 for HIV-infected cells.

Because only a small percentage of the cells were actually infected with HIV, the HIV strain was modified to permit labeling of infected cells so as to distinguish them from uninfected cells in the putatively infected cell population. To this end, the amino terminal portion of the nef gene was deleted and replaced by the murine thymocyte surface antigen Thy 1.2 by inserting the cDNA of this gene at the XhoI and MluI restriction sites, thus obtaining the plasmid pNL-Thy. Viral stocks of the marked NL-Thy virus were prepared as described except that the plasmid pNL-Thy was used for transfaction. Since the surface antigan shows efficient surface expression and can be labeled with an antibody, it was a convenient marker for cells infected by the modified HIV-1.

The successfully infected cells exhibiting Thy 1.2 surface antigen at the surface were sorted into positive and negative subpopulations and analyzed by quantitative PCR. Quantitative PCR amplification with $^{32}$P end-labeled primers was performed as previously described (Arrigo, S. J. et al. *J Virol* (1989) 63: 4875–4881; Lee, M. et al. *Science* (1989) 244: 431–475; Peng, S. et al. *Nature* (1990) 343: 85–89; Zack, J. A. et al. *Cell* (1990) 61: 213–222; Zack, J. A. et al. *J Virol* (1992) 66: 1717–1725). Amplification (30 cycles) was performed for HIV-1 and human β-globin sequence analysis by using radiolabeled oligonucleotide primers. The β-globin specific primers and the HIV-1 LTR-specific primers (M667 and AA55), were used as described elsewhere (Zack, J. A. et al. (1990) (supra)). Following amplification, the radiolabeled products were resolved on 6% polyacrylamide gel (PAGE) and visualized by autoradiography. HIV-1 DNA standards used to quantitate viral DNA were derived from dilutions of cloned HIV-1 JR CSF DNA (Cann, A. J. et al. J Virol (1988) 64: 4735–4742) and digested with EcoRI, which does not cleave viral sequences. This DNA was diluted into PBL DNA at 10 µg/ml. Standard curves for β-globin DNA were derived from dilutions of PBL DNA.

Only a small percentage of Thy $1.2^-$ cells appeared to be infected. The entire Thy $1.2^+$ population contained the correct amount of HIV proviral DNA. Histograms obtained using cell flow cytometry confirmed that the infected Thy $1.2^+$ population was G2 arrested, while the Thy $1.2^-$ population was not.

Detection of cells bearing the surface marker Thy 1.2 was as follows: $1\times10^6$ cells were harvested and stained in 100 µl of Thy 1.2 FITC conjugated monoclonal antibody (Caltag, Calif. Cat. No. MM2001-3) diluted 1/200 in FACS buffer (PBS with 2% FCS and 0.01% sodium azide) for 20 minutes at 4° C. An additional sample of cells was stained with the isotype antibody IgG2b-FITC (Caltag, Calif. Cat. No. MG2B01), to control for non-specific background antibody binding. The cells were then washed and resuspended in FACS buffer containing 1 µg/ml P1 and analyzed as above. Green FITC fluorescence was collected after a 530/30 nm BP filter and was displayed on a four decade log scale, while orange P1 fluorescence was collected as above but displayed on a log scale. Electronic compensation was used among the fluorescence channels to remove residual spectral overlap. The use of P1 as a vital dye allows dead cells to be excluded from the population during analysis reducing the background of non-specific antibody binding.

The method of dual staining for surface antigen and DNA content of cells was adapted from the technique of Schmidt, et al. Cytometry (1991) 12: 279–285. Briefly, $1\times10^6$ cells were harvested and stained as above for Thy 1.2 surface antigen. After washing, the cells were fixed in PBS with 0.3% paraformaldehyde for 1 hour at 4° C. Cells were subsequently permeabilized in 0.2% Tween-20 (Bio-Rad. Cat. No. 170-6531) in PBS at 4° C. for 15 minutes, and the DNA finally stained in FACS buffer containing 10 µg/ml P1 and 11.25 Kunitz units of ribonuclease A for 30 minutes at 4° C. At least 5000 events were collected as described above.

The time course for this perturbation of the cell cycle was also determined for the Thy $1.2^+$ infected cells. At day 1 postinfection the ratio of G1 to G2/M cells was 1.3 for Thy $1.2^+$ cells and 2.3 for Thy $1.2^-$ cells; this ratio fell to 0.49 on day 2 for the Thy $1.2^+$ cells and remained at this level for the remainder of the experiment. The Thy $1.2^-$ cells maintained the ratio of approximately 2.0 for the remainder of the experiment as well. The time period for this experiment was four days altogether.

This was true despite the fact that the percentage of Thy $1.2^+$ cells in the culture rose from 3.3% on day 1 to 59% on day 4. The noninfected subpopulation remaining still exhibited the normal cell cycle profile. The cytopathic effect exhibited in the infected cells prevented continuing the experiment for more than five days. The results are summarized in Table 1.

TABLE 1

| | | Thy 1− | | | Thy 1+ | | |
|---|---|---|---|---|---|---|---|
| Day | % Thy+ | % G1 | % G2 | G1/G2 Ratio | % G1 | % G2 | G1/G2 Ratio |
| 1 | 3.3 | 67 | 29 | 2.3 | 2.4 | 1.9 | 1.3 |
| 2 | 6.1 | 61 | 33 | 1.9 | 1.9 | 3.9 | 0.49 |
| 3 | 14 | 60 | 25 | 2.4 | 5.9 | 9.1 | 0.65 |
| 4 | 59 | 30 | 17 | 1.8 | 17 | 35 | 0.49 |

Similar experiments were run in the presence of anti-AIDS drugs including the reverse transcription inhibitor AZT, the protease inhibitor A77003 described by Kaplan, A. et al. J Virol (1993) 67: 4050 and by Jaskolski, M. et al. Biochemistry (1991) 30: 1600–1609; and soluble CD4. These drugs succeeded in preventing the spread of infection from the initially affected Thy $1.2^+$ cells through the culture. However, the cells that were Thy $1.2^+$ remained perturbed in their cell cycles wherein about 90% of these cells were in the G2 compartment over a period of three days.

This experiment was repeated using $CD4^+$-enriched peripheral blood lymphocytes (PBLs) rather than the leukemic SupT1 cell line. PBLs were enriched to 85–90% $CD4^+$ by negative selection panning and used as target cells for infection by the Thy 1.2-labeled HIV vectors. Peripheral blood lymphocytes (PBL) were obtained from normal donors by venipuncture, isolated by centrifugation over Ficoll-Hypaque (Pharmacia, Sweden; Cat. No. 17-0840-03), and depleted of macrophages by adherence to plastic for four hours. The lymphocytes were then cultured in the presence of phytohemagglutinin (PHA; HA15, 0.8 µg/ml; Wellcome) for three days prior to infection. The culture was enriched for the $CD4^+$ population by negative selection panning (Wysocki, Proc Natl Acad Sci USA (1978) 75: 2844–2848) using anti-CD8 (OKT8) and anti-CD11 b (OKM1) antibodies. These antibodies were prepared from hybridoma cell lines obtained from ATCC (OKT8 Cat. No. CRL 8014 and OKM1 Cat. No. CRL 8026). Levels of CD4 cells were determined pre-and post-panning by staining with anti-CD4 antibodies (Becton-Dickinson, San Jose, Calif. Cat. No. 347323) conjugated to fluorescein isothiocyanate (FITC), and flow cytometry as described above. Following infection, these cells were cultured in RPMI supplemented with 10% fetal calf serum and 30 U/ml of recombinant interleukin 2 (rIL-2; AMGEN, Thousand Oaks, Calif. Cat. No. 5724-95D) with antibiotics as above. The results are shown in Tables 2–4.

TABLE 2

| | Culture Kinetics | |
|---|---|---|
| Day | % Thy 1+ | p24 ng/ml |
| 1 | 2.9 | 1.9 |
| 2 | 5.8 | 24 |
| 3 | 7.6 | 266 |
| 4 | 12 | 264 |

TABLE 3

| | Mock Infected | | |
|---|---|---|---|
| Day | % G1 | % G2 | G1/G2 |
| 1 | 65 | 33 | 2.0 |
| 2 | 70 | 28 | 2.5 |
| 3 | 77 | 23 | 3.3 |
| 4 | 82 | 18 | 4.6 |

TABLE 4

| | NL-Thy Infected | | | | | |
|---|---|---|---|---|---|---|
| | Uninfected Subpopulation (Thy 1⁻) | | | Infected Subpopulation (Thy 1⁺) | | |
| Day | % G1 | % G2 | G1/G2 | % G1 | % G2 | G1/G2 |
| 1 | 65 | 29 | 2.2 | 1.9 | 2.6 | 0.73 |
| 2 | 61 | 27 | 2.3 | 3.9 | 7.6 | 0.51 |
| 3 | 67 | 21 | 3.2 | 3.9 | 7.7 | 0.51 |
| 4 | 70 | 13 | 5.4 | 6.5 | 10 | 0.65 |

The ratio of G0/G1 to G2/M in mock-infected cultures and in the Thy $1.2^-$ subpopulation of the infected culture increased from 2.0 on day 1 to 5.0 on day 4. This ratio is higher than observed for the leukemic cells; however, the Thy $1.2^+$ subpopulation again demonstrated G2 arrest wherein the ratio of G0/G1 to G2/M was in the range of 0.1–0.73 during all three days of the experiment. G2 arrest occurring in PBL in vivo would prevent proliferation of an activated T cell and thus have a devastating effect on cellular immunity.

EXAMPLE 2

Infection with Vpr Deficient Mutant HIV

The HIV modified Thy vector contains a unique EcoRI restriction enzyme site in the Vpr open reading frame so that mutating this vector to eliminate Vpr expression was straightforward. The vector was digested with EcoRI, filled in with Klenow and religated creating a frame shift to the +1 reading frame at amino acid position 64. This deleted the carboxy terminal 33 amino acids of Vpr and added 16 additional residues before the stop codon. The resulting retroviral vector was then used to produce viral stocks of "Vpr-X Virus".

In more detail, the nef open reading frame of pNL4-3 was deleted from the Xho I to Kpn I sites and replaced with the coding sequence for the murine thymocyte surface antigen Thy 1.2 to obtain pNL-Thy (Giguere, V. et al. *EMBO J* (1985) 4: 2017–2024). The Vpr-X mutant virus was obtained by cleaving the pNL-Thy with EcoRI (nucleotide position 132 of the Vpr open reading frame) blunt ending by filling in with the DNA polymerase I Klenow fragment and religating according to standard procedures. The resulting frameshift replaced the carboxy terminal 33 residues of the 97 amino acid Vpr protein with the sequence: NSAT-TAVYPFQNWVST.

The Vpr-X virus was then used to infect SupT1 cell cultures in parallel with the HIV Thy-containing virus. Infection was at an equivalent multiplicity of infection. Samples were recovered from both cultures at 24-hour intervals and assayed for the spread of the virus. The proportion of infected cells rose in cultures infected with either the HIV-containing Thy or Vpr-X infected cultures, but over days 3–5, the rate of spread was marginally higher in the Thy-containing cultures than in Vpr-X, reaching 26% and 12% respectively.

Cell flow cytometry was then used to determine the G1/G2 ratios of each infected culture. Cells infected with Vpr-X no longer exhibited the G2 arrest phenotype, as shown in Tables 5–8.

TABLE 5

| | Culture Kinetics | | | |
|---|---|---|---|---|
| | % Thy 1⁺ | | p24 ng/ml | |
| Day | NL-Thy | Vpr-X | NL-Thy | Vpr-X |
| 1 | 1.0 | 1.0 | 1.0 | 0.6 |
| 2 | 1.4 | 1.4 | 8.0 | 3.0 |
| 3 | 2.5 | 2.2 | 25 | 13 |
| 4 | 5.7 | 3.7 | 115 | 81 |
| 5 | 26 | 12 | 640 | 320 |

TABLE 6

| | Mock Infected | | |
|---|---|---|---|
| Day | % G1 | % G2 | G1/G2 |
| 1 | 56 | 38 | 1.5 |
| 2 | 71 | 29 | 2.4 |
| 3 | 69 | 31 | 2.2 |
| 4 | 70 | 30 | 2.3 |
| 5 | 69 | 31 | 2.2 |

TABLE 7

| | NL-Thy Infected Culture | | | | | |
|---|---|---|---|---|---|---|
| | Uninfected Subpopulation (Thy 1⁻) | | | Infected Subpopulation (Thy 1⁺) | | |
| Day | % G1 | % G2 | G1/G2 | % G1 | % G2 | G1/G2 |
| 1 | 57 | 38 | 1.5 | 0.72 | 0.77 | 0.94 |
| 2 | 71 | 28 | 2.5 | 0.51 | 1.1 | 0.46 |
| 3 | 71 | 26 | 2.7 | 0.80 | 1.7 | 0.47 |
| 4 | 62 | 19 | 3.3 | 2.1 | 2.8 | 0.75 |
| 5 | 42 | 35 | 1.2 | 9.5 | 14 | 0.68 |

TABLE 8

| | Vpr-X Infected Culture | | | | | |
|---|---|---|---|---|---|---|
| | Uninfected Subpopulation (Thy 1⁻) | | | Infected Subpopulation (Thy 1⁺) | | |
| Day | % G1 | % G2 | G1/G2 | % G1 | % G2 | G1/G2 |
| 1 | 62 | 37 | 1.7 | 0.54 | 0.50 | 1.1 |
| 2 | 64 | 34 | 1.9 | 1.0 | 0.70 | 1.4 |
| 3 | 65 | 32 | 2.0 | 1.9 | 1.1 | 1.7 |
| 4 | 71 | 25 | 2.8 | 2.9 | 1.5 | 1.9 |
| 5 | 56 | 33 | 1.7 | 6.2 | 4.2 | 1.5 |

EXAMPLE 3

Effect of Vpr Protein Alone on the Cell Cycle

A vector was constructed containing Thy 1.2 under control of the CMV immediate early promoter as well as an expression system for the Vpr open reading frame under the control of another copy of the CMV promoter. This vector, BSVprThy, would effect expression of both Thy and Vpr in transfected host cells. A control plasmid (BSThy) differs from BSVprThy only in lacking the Vpr open reading frame.

The expression plasmids were constructed to contain the Thy 1.2 and the Vpr (derived from HIV-1 NL 4 3) open reading frames both driven by the CMV immediate early promoter. Briefly the Thy 1.2 open reading frame was amplified by PCR from a cDNA library. A mouse thymoma cell line cDNA library obtained from Brian Seed, Harvard University, was used as a template for PCR using primers of the following sequences:

5'-CAAGTCGGAACTCGAGGCACCATGAAC-3' (sense) and
5'-CGCGGTACCACGCGTCACAGAGAAATGAAGTC-TAG-3' (antisense)

which are complementary to the 5' and 3' ends of the Thy-1 coding sequences and extended to include XhoI site at the 5'-terminus and MluI and KpnI sites at the 3'-terminus. The amplified DNA was digested with XhoI and MluI and ligated into pCMV (Planelies, V. et al. *AIDS Res Hum Retroviruses* (1991) 7: 889) expression vector flanked by the CMV immediate early promoter and the SV40 polyA sequence to provide transcriptional termination sequences and generate pCMV-Thy. The transcriptional unit was then transferred into the Bluescript® II KS$^+$ plasmid (Stratagene La Jolla, Calif. Cat. No. 212207). The Vpr open reading frame was first cloned into the pCDM8 (Invitrogen, San Diego, Calif. Cat. No. V308-20) expression vector from pNL4-3. The transcriptional cassette containing the CMV immediate early promoter and the HIV 3'LTR transcriptional termination sequences were transferred into the above Bluescript vector containing the thy 1.2 expression cassette. A control vector was constructed by subcloning the Thy expression cassette into CDM8 alone (lacking the Vpr open reading frame).

In more detail an SpeI/XhoI fragment of pCDM8 (Invitrogen, San Diego, Calif.) containing the CMV immediate early promoter was inserted into SpeI/XhoI digested NL-Thy (Plannelles et al., 1994, manuscript in preparation) to obtain the plasmid NL-CMV-Thy. NL-Thy contains the open reading frame for Vpr and the Thy 1.2 open reading frame prepared as described above. Digestion of NL-CMV-Thy resulted in a fragment containing the CMV promoter, the Thy 1.2 open reading frame and the 3' LTR sequences from HIV. This fragment was transferred to PstI digested Bluescript® II KS Plus (Stratagene, La Jolla, Calif.) to obtain BS-CMV-Thy.

The Vpr open reading frame was obtained by digesting pNL4-3 (Adachi et al., 1986 (supra)) with ScaI and SacI. The ScaI/SacI fragment was cloned into SmaI/SacI cleaved plasmid pGEM7Zf(−) (Promega Madison, Wis.) to obtain pGEM-Vpr. PGEM-Vpr was digested with XhoI and NsiI and the resulting fragment cloned into XhoI/PstI digested pCDM8 to obtain CDMS-Vpr.

A NruI to BamHI fragment of CDM8-Vpr containing the CMV promoter, Vpr open reading frame and SV40 transcription termination sequences was cloned into BS-CMV-Thy described above digested with NotI, blunt ended by filing in, and with BamHI to obtain BS-Vpr-Thy. The control plasmid BS-Thy was constructed by cloning the NruI/BamHI fragment of pCDM8 containing only the CMV promoter and SV40 transcriptional termination sequences into BS-CMV-Thy digested with NotI, blunt ended by filing in and with BamHI. All cloning steps described followed standard procedures.

Plasmid DNA was prepared for transfection by purification on an anion exchange resin (Qiagen Chatsworth, Calif. Cat. No. 12145) following the manufacturers protocol. HeLa cells (human epithelial fibroblast; ATCC CCL 2) and COS cells (African green monkey kidney fibroblast; ATCC CRL 1651) were grown in DMEM with 10% calf serum (Gemini, Calabasas, Calif. Cat. No. 100-102). 10 μg of plasmid DNA was added to 5×10$^6$ cells in electroporation media. Electroporation conditions for SupT1 cells was as described above for MT2 cells, and for COS and HeLa cells was 250 V at 960 pLF.

Cells were harvested at 48 hrs post transfection and stained as described above for presence of Thy 1.2 surface antigen and cell cycle phase determination. SupT1 cells, COS cells and HeLa cells were transfected with either the control vector or the vector expressing Vpr. The pattern of G2 arrest in labeled Thy 1.2$^+$ cells transfected with the Vpr-containing vector was maintained as shown in Table 9.

TABLE 9

| Cell Line | G1/G2 Ratio | | G1/G2 Ratio | |
|---|---|---|---|---|
| | Thy 1.2$^-$ | Thy 1.2$^+$ | Thy 1.2$^-$ | Thy 1.2$^+$ |
| SupT1 | 1.3 | 1.3 | 1.2 | 0.67 |
| HeLa | 1.6 | 2.3 | 1.7 | 0.32 |
| COS-6 | 2.2 | 12.5 | 2.2 | 0.54 |

These results show that Vpr is able to induce G2 cell arrest in cells generally, and this function of the protein is not dependent on HIV infection.

We claim:

1. A method to identify a compound that blocks Vpr mediated cell cycle statis, said method comprising the steps of:

a) contacting a compound to be tested with a Vpr protein;

b) determining whether said compound binds to said Vpr protein;

c) identifying a compound that binds to said Vpr protein;

d) culturing cells in the presence and absence of said compound of step (c), said cells having been modified to contain an expression system that encodes a Vpr protein, under conditions in which the Vpr protein is expressed and blocks cell division;

e) measuring an indicator of cell replication of the cells that were cultured in the presence and absence of said compound;

f) identifying a compound that can block HIV mediated cell cycle arrest by selecting a compound in which cell replication in the presence of said compound is greater than in the absence of said compound.

2. The method of claim 1, wherein said Vpr protein is an HIV Vpr protein.

3. The method of claim 1, wherein said cell is a eukaryotic cell.

4. The method of claim 3, wherein said eukaryotic cell contains an exogenously supplied DNA molecule that constitutively expresses the Vpr protein.

5. The method of claim 3, wherein said eukaryotic cell contains an exogenously supplied DNA molecule that inducibly expresses the Vpr protein.

6. The method of claim 3, wherein said eukaryotic cell contains an exogenously supplied DNA molecule that transiently expresses the Vpr protein.

* * * * *

UNITED STATES PATENT AND TRADEMARK OFFICE
CERTIFICATE OF CORRECTION

PATENT NO. : 5,721,104

DATED : February 24, 1998

INVENTOR(S) : Irvin S. Y. Chen et al.

It is certified that error appears in the above-identified patent and that said Letters Patent is hereby corrected as shown below:

In column 1, lines 5-11, please delete:

ACKNOWLEDGEMENT OF GOVERNMENT SUPPORT
The work described herein was funded in part by a grant from the National Institutes of Health No. C930122. The U.S. government has certain rights in this invention.

Signed and Sealed this

Fifteenth Day of June, 1999

Attest:

Q. TODD DICKINSON

*Attesting Officer*    Acting Commissioner of Patents and Trademarks